(12) United States Patent
Berglund

(10) Patent No.: US 7,815,962 B2
(45) Date of Patent: Oct. 19, 2010

(54) COATED STENT WITH EVENLY DISTRIBUTED THERAPEUTIC AGENT

(75) Inventor: Joseph Berglund, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 674 days.

(21) Appl. No.: 11/690,000

(22) Filed: Mar. 22, 2007

(65) Prior Publication Data

US 2008/0233267 A1  Sep. 25, 2008

(51) Int. Cl.
*A61L 33/00* (2006.01)
*B05D 3/02* (2006.01)
*B05D 3/10* (2006.01)
*A61F 2/06* (2006.01)

(52) U.S. Cl. .............. 427/2.1; 427/2.24; 427/2.25; 427/257; 427/261; 427/270; 427/271; 623/1.2; 623/1.43; 623/1.46

(58) Field of Classification Search ............ 427/2.1, 427/2.24, 2.25, 257, 261, 264, 270, 271; 623/1.2, 1.43, 1.46
See application file for complete search history.

(56) References Cited

U.S. PATENT DOCUMENTS

| | | | | |
|---|---|---|---|---|
| 5,605,696 A * | 2/1997 | Eury et al. | | 424/423 |
| 5,824,048 A * | 10/1998 | Tuch | | 128/898 |
| 5,980,972 A * | 11/1999 | Ding | | 427/2.24 |
| 6,103,295 A | 8/2000 | Chan et al. | | |
| 6,346,110 B2 | 2/2002 | Wu | | |
| 6,709,449 B2 | 3/2004 | Camrud et al. | | |
| 6,726,829 B2 | 4/2004 | Trozera | | |
| 7,285,304 B1 * | 10/2007 | Hossainy et al. | | 427/2.24 |
| 2004/0098118 A1 * | 5/2004 | Granada et al. | | 623/1.42 |
| 2005/0239508 A1 * | 10/2005 | Schwarz et al. | | 455/562.1 |
| 2005/0241668 A1 | 11/2005 | Trampuz et al. | | |
| 2007/0055349 A1 * | 3/2007 | Santos et al. | | 623/1.15 |
| 2008/0097569 A1 * | 4/2008 | O'Connor et al. | | 623/1.2 |

* cited by examiner

Primary Examiner—Frederick J Parker
Assistant Examiner—Cachet I Sellman

(57) ABSTRACT

A stent includes a stent framework and a coating disposed on the stent framework. The coating includes an inner surface and an outer surface. The coating has a circumferential therapeutic concentration zone near the inner surface and a circumferential washed zone near the outer surface.

2 Claims, 8 Drawing Sheets

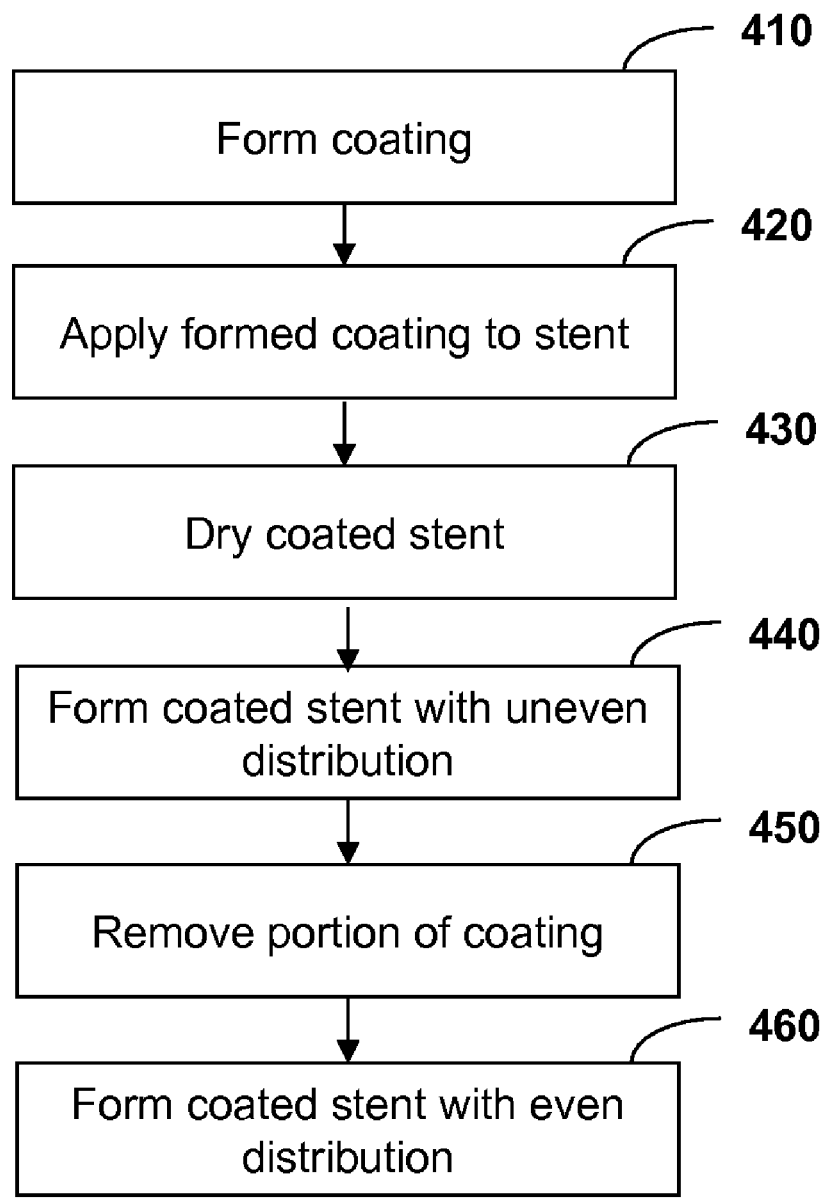

Distance from stent surface

Distance from stent surface

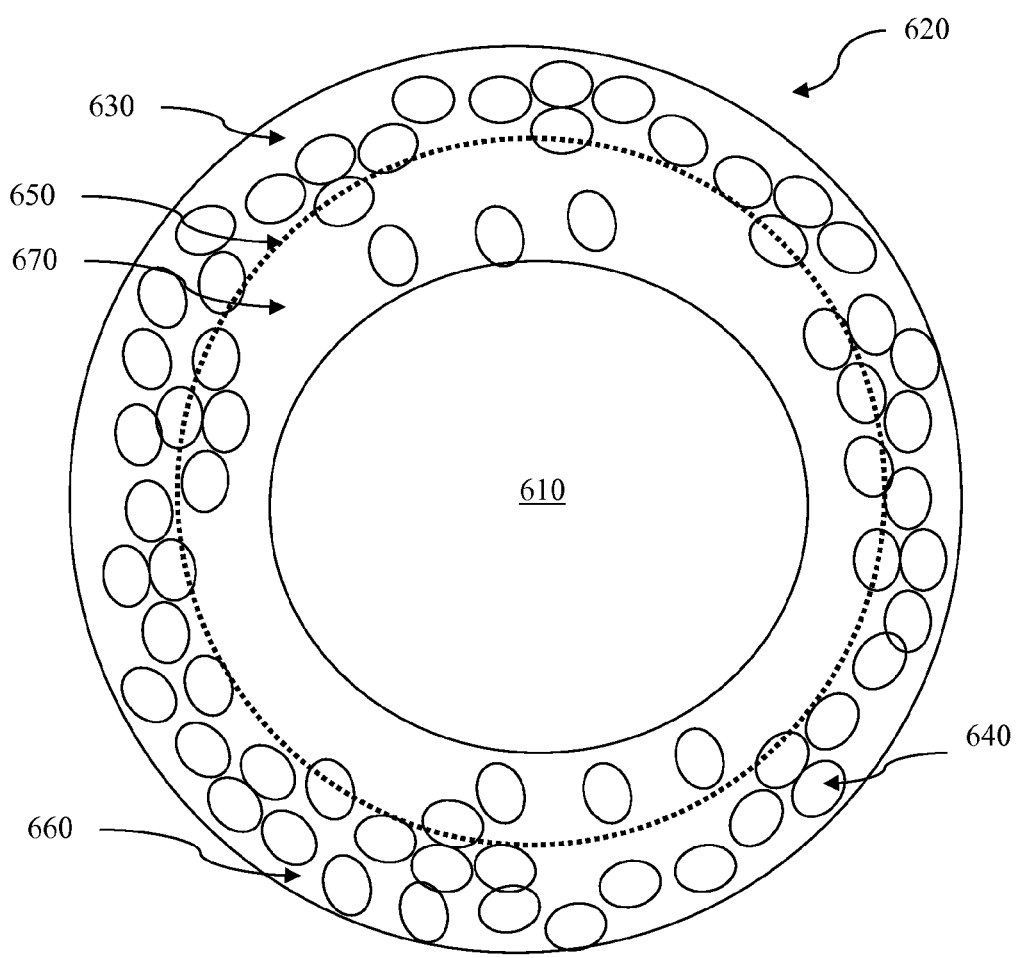

US 7,815,962 B2

COATED STENT WITH EVENLY DISTRIBUTED THERAPEUTIC AGENT

TECHNICAL FIELD

This invention relates generally to medical devices for treating vascular problems, and more particularly to a coated stent.

BACKGROUND OF THE INVENTION

Drug eluting stents have become popular medical devices. One difficulty with such devices is the difficulty in binding the drug to the stent and controlling drug elution. Previously, this problem has been addressed by incorporating the drug, often rapamycin, sirolimus, or the like, within a carrier and layering the drug carrier on a stent surface.

The carrier coating process generally requires a solvent, in which the drugs are usually soluble, and it is therefore desirable to provide a drug coated stent without polymeric vehicles to deliver the drug.

The biocompatibility of polymers has come into question. A degradable coating may provide biocompatibility advantages over permanent polymer coatings in allowing the tissue to eventually come into direct contact with the bulk stent material.

Additionally, carriers and therapeutic agents dry at different rates or are carried with the solvent as the solvent diffuses through the carrier. This results in formation of a concentration gradient through the thickness of the coating, as the carrier dries first, forcing the still wet therapeutic agent to the outer edges of the coating. While the coating still contains the same amount of the drug, the resulting concentration of the therapeutic agent near the outer surface of the coated stent can result in a "drug burst" on deployment. This drug burst must be considered when establishing dosage and elution characteristics.

It would be desirable, therefore, to provide a coated stent that would overcome the limitations and disadvantages inherent in the devices described above.

SUMMARY OF THE INVENTION

A first aspect of the invention provides a stent. The stent includes a stent framework and a coating disposed on the stent framework, the coating having an inner surface and an outer surface, the coating having a circumferential therapeutic concentration zone near the inner surface and a circumferential washed zone near the outer surface.

Another aspect of the invention provides a method of manufacturing a coated stent that includes forming a coating including at least one carrier and at least one therapeutic agent and applying the formed coating to the stent. The method further includes drying the coated stent, forming a coated stent, removing a portion of the applied coat, and forming a coated stent wherein the at least one therapeutic agent is substantially evenly distributed within the carrier.

Another aspect of the invention provides a system for treating a vascular condition. The system includes a catheter and a stent carried on the catheter. The stent includes a stent framework and a coating disposed on the stent framework. The coating includes at least one carrier and at least one therapeutic agent substantially evenly distributed throughout the carrier.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The drawings are not to scale. The foregoing aspects and other attendant advantages of the present invention will become more readily appreciated by the detailed description taken in conjunction with the accompanying drawings.

BRIEF DESCRIPTION OF THE DRAWINGS

FIG. 4 is a flow diagram of a method of manufacturing a coated stent, in accordance with one embodiment of the current invention;

FIG. 6A, FIG. 6B, and FIG. 6C illustrate cross sections of a coated stent before and after removal of a portion of the coating, in accordance with one aspect of the invention.

DETAILED DESCRIPTION

The invention will now be described by reference to the drawings wherein like numbers refer to like structures.

Figure 1:
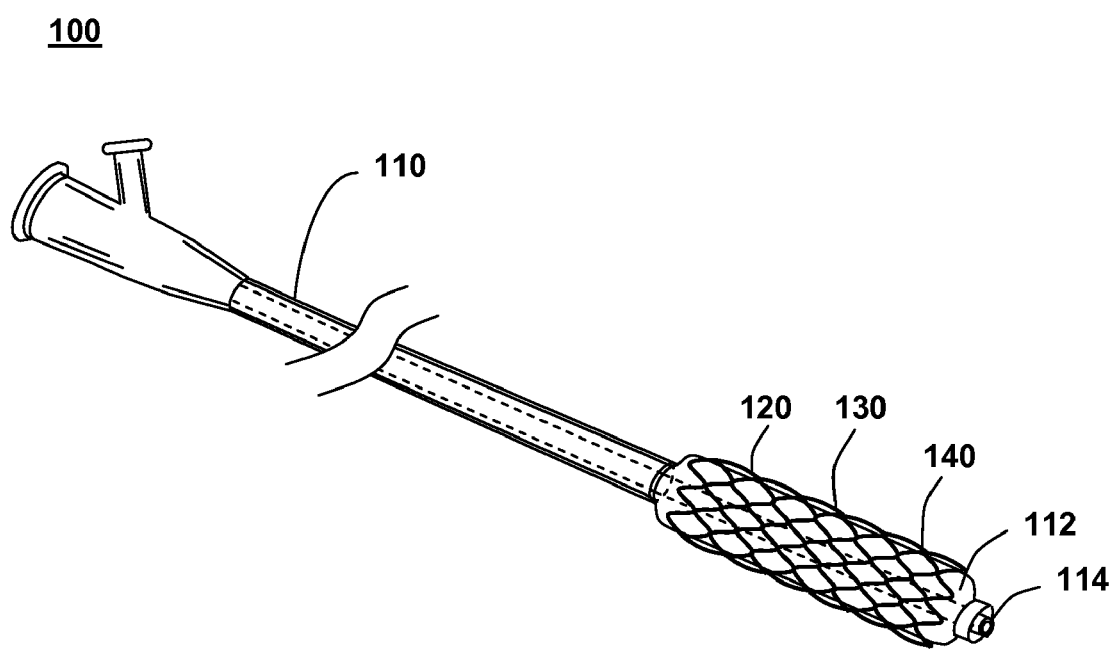
FIG. 1 is an illustration of a system for treating a vascular condition including a coated stent coupled to a catheter, in accordance with one embodiment of the current invention.

FIG. 1 shows an illustration of a system for treating a vascular condition, comprising a coated stent coupled to a catheter, in accordance with one embodiment of the present invention at 100. System 100 includes a coated stent 120 coupled to a delivery catheter 110. Coated stent 120 includes a stent framework 130 and a coating 140 disposed on the stent framework. Coating 140 includes at least a first therapeutic agent. In certain embodiments, coating 140 includes at least two therapeutic agents—a first therapeutic agent and a second therapeutic agent for example.

Insertion of coated stent 120 into a vessel in the body helps treat, for example, heart disease, various cardiovascular ailments, and other vascular conditions. Catheter-deployed coated stent 120 typically is used to treat one or more blockages, occlusions, stenoses, or diseased regions in the coronary artery, femoral artery, peripheral arteries, and other arteries in the body. Treatment of vascular conditions may include the prevention or correction of various ailments and deficiencies associated with the cardiovascular system, the cerebrovascular system, urinogenital systems, biliary conduits, abdominal passageways and other biological vessels within the body.

An exemplary coating 140 includes or encapsulates one or more therapeutic agents. Coating 140 may comprise one or more therapeutic agents dispersed within or encased by drug layers or barrier layers, such as an intermediate layer, on coated stent 120. These drug layers and therapeutic agents are eluted or leached from coated stent 120 with, for example, controlled time delivery after deployment of coated stent 120 into the body. A therapeutic agent is capable of producing a beneficial effect against one or more conditions including coronary restenosis, cardiovascular restenosis, angiographic restenosis, arteriosclerosis, hyperplasia, and other diseases or conditions. For example, the therapeutic agent can be selected to inhibit or prevent vascular restenosis, a condition corresponding to a narrowing or constriction of the diameter of the bodily lumen where the stent is placed. Coating 140 may comprise, for example, an antirestenotic agent such as rapamycin, a rapamycin derivative, or a rapamycin analog such as everolimus or zotarolimus to prevent or reduce the recurrence of narrowing and blockage of the bodily vessel. Coating 140 may comprise an anti-cancer drug such as paclitaxel or camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or a combination thereof. In one example, a first therapeutic agent comprises an antirestenotic drug such as rapamycin, a rapamycin derivative, or a rapamycin analog such as everolimus or zotarolimus. The second therapeutic agent may comprise, for example, an anti-cancer drug such as paclitaxel or camptothecin or other topoisomerase inhibitors. The therapeutic agent constituency in the drug layers may be, for example, between 0.1 percent and 50 percent of the drug layer by weight. In another example, the first therapeutic agent comprises an anti-proliferative compound such as 5-fluorouracil, with an optional second therapeutic agent such as rapamycin, a rapamycin derivative, a rapamycin analog such as everolimus or zotarolimus, or dexamethosone. In another example, the first therapeutic agent comprises an anti-inflammatory such as dexamethasone, and an optional second therapeutic agent such as 5-fluorouracil.

In one example, a first therapeutic agent comprises an antirestenotic drug such as rapamycin, a rapamycin derivative, or a rapamycin analog such as everolimus or zotarolimus. The second therapeutic agent may comprise, for example, an anti-cancer drug such as paclitaxel or camptothecin or other topoisomerase inhibitors. The therapeutic agent constituency in the drug layers may be, for example, between 0.1 percent and 50 percent of the drug layer by weight. In another example, the first therapeutic agent comprises an anti-proliferative compound such as 5-fluorouracil, with an optional second therapeutic agent such as rapamycin, a rapamycin derivative, a rapamycin analog, or dexamethosone. In another example, the first therapeutic agent comprises an anti-inflammatory such as dexamethasone, and an optional second therapeutic agent such as 5-fluorouracil.

As used herein, the term carrier is any substrate used to carry the therapeutic agent. The carrier can be a bio-absorbable polymer, a bioactive polymer, a sugar such as dextran, a protein, a bio-protein, or the like. In other embodiments, the term "carrier" includes metallic substances, such as magnesium, carbon, boron, or the like. The figures herein, where illustrating physical structures, are not drawn to scale.

The term "therapeutic agent" includes one or more "therapeutic agents" or "drugs." The terms "therapeutic agents" and "drugs" are used interchangeably and include pharmaceutically active compounds, nucleic acids with and without carrier vectors such as lipids, compacting agents (such as histones), virus (such as adenovirus, adeno-associated virus, retrovirus, lentivirus and a-virus), polymers, antibiotics, hyaluronic acid, gene therapies, proteins, cells, stem cells and the like, or combinations thereof, with or without targeting sequences. Specific examples of therapeutic agents include, for example, pharmaceutically active compounds, proteins, cells, stem cells, oligonucleotides, ribozymes, antisense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a noninfectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, everolimus or zotarolimus, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/antimitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, dephalosporins, aminoglycosides, and nitorfurantoin; anesthetic agents such as lidocaine, buplvacaine, and ropivacaine; nitrix oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Alternatively, the therapeutic agent may comprise, for example, an antirestenotic agent such as rapamycin, a rapamycin derivative, or a rapamycin analog such as everolimus or zotarolimus to prevent or reduce the recurrence of narrowing and blockage of the bodily vessel. Therapeutic agent may comprise an anti-cancer drug such as paclitaxel, camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or a combination thereof. In one example, a first therapeutic agent comprises an antirestenotic drug such as rapamycin, a rapamycin derivative, or a rapamycin analog such as everolimus or zotarolimus. The therapeutic agent constituency in the coating may be, for example, between 0.1 percent and 50 percent of the coating by weight. In another example, the therapeutic agent comprises an anti-proliferative compound such as 5-fluorouracil, with an optional second therapeutic agent such as rapamycin, a rapamycin derivative, a rapamycin analog such as everolimus or zotarolimus, or dexamethosone. In another example, the first therapeutic agent comprises an anti-inflammatory such as dexamethasone, and an optional second therapeutic agent such as 5-fluorouracil.

The elution rates of the therapeutic agents and total drug eluted into the body and the tissue bed surrounding the stent framework are responsive to the target thickness of coating 140, the constituency and individual layer thicknesses of coating 140, the nature and concentration of the therapeutic agents, the thickness, composition, and degradation rate of any intermediate coat, the total number of layers of successive therapeutic and intermediate layers, and other factors including location of the coating on the stent, deployment position, and the like. Coating 140 may include and elute or leach multiple therapeutic agents to achieve the desired therapeutic effect.

Catheter 110 of an exemplary embodiment of the present invention includes a balloon 112 that expands and deploys the stent within a vessel of the body. After positioning coated stent 120 within the vessel with the assistance of a guide wire traversing through a guidewire lumen 114 inside catheter 110, balloon 112 is inflated by pressurizing a fluid such as a contrast fluid or saline solution that fills a tube inside catheter 110 and balloon 112. Coated stent 120 is expanded until a desired diameter is reached, and then the fluid is depressurized or pumped out, separating balloon 112 from coated stent 120 and leaving coated stent 120 deployed in the vessel of the body. Alternately, catheter 110 may include a sheath that retracts to allow expansion of a self-expanding version of coated stent 120.

Figure 2:
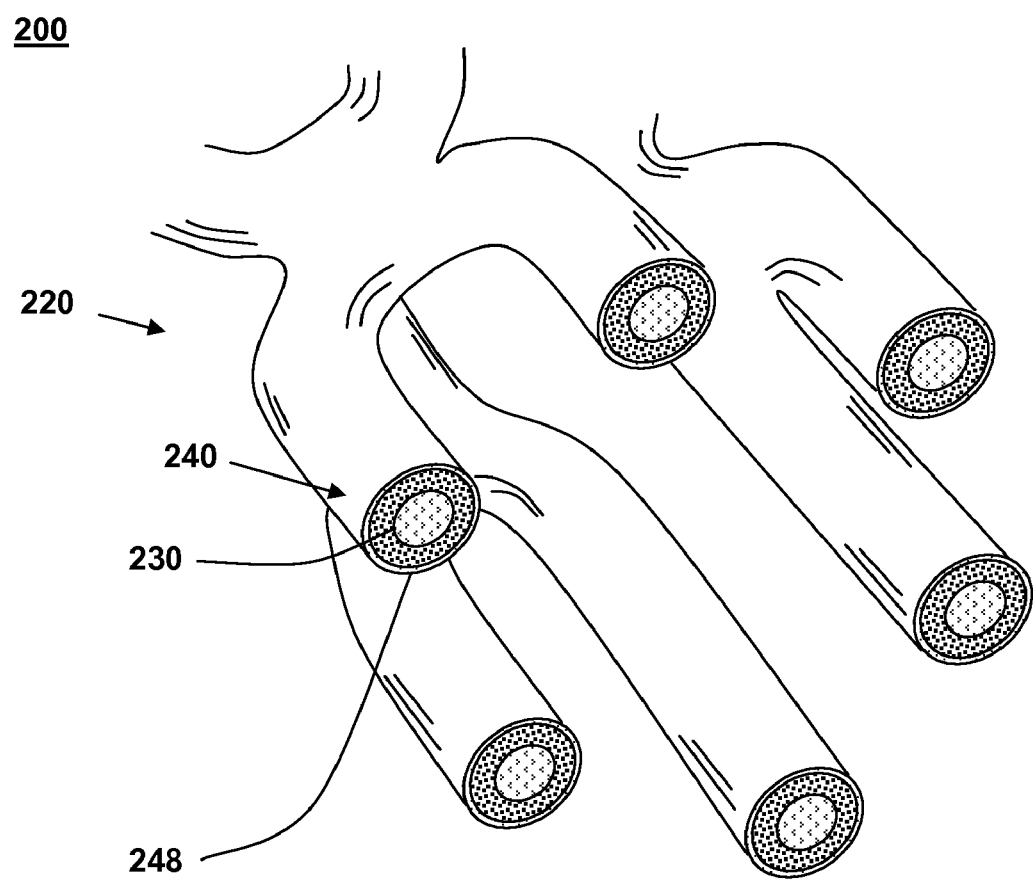
FIG. 2 is a cross-sectional perspective view of a coated stent, in accordance with one embodiment of the current invention.

FIG. 2 shows a cross-sectional perspective view of a coated stent, in accordance with one embodiment of the present invention at 200. A coated stent 220 includes a stent framework 230 with a coating 240 disposed on stent framework 230. In certain embodiments, drug coating 240 includes at least a first therapeutic agent, and at least one carrier. In one embodiment, the coating layers are sputter coats. In other embodiments, the coating is applied using another appropriate technique, such as vacuum deposition, electrolytic deposition, electroless deposition, electrostatic deposition, or the like. In one embodiment, the coating layer is a topcoat.

Although illustrated with two sets of drug layers and coating layers, multiple sets of coating layers may be disposed on stent framework 230. For example, ten sets of layers, each layer on the order of 0.1 micrometers thick, can be alternately disposed on stent framework 230 to produce a two-micrometer thick coating. In another example, twenty sets of layers, each layer on the order of 0.5 micrometers thick, can be alternately disposed on stent framework 230 to produce a twenty-micrometer thick coating. The drug layers and the coating layers need not be the same thickness, and the thickness of each may be varied throughout drug coating 240.

Stent framework 230 comprises a metallic base or a polymeric base, such as stainless steel, nitinol, tantalum, MP35N alloy, platinum, titanium, a chromium-based alloy, a suitable biocompatible alloy, a suitable biocompatible material, a biocompatible polymer, or a combination thereof. In certain embodiments featuring the stent framework comprises any suitable polymer for biomedical stent applications, as is known in the art. Suitable polymers include polycaprolactone, polylactide, polyglycolide, polyorthoesters, polyanhydrides, poly(amides), poly(trimethylene carbonates), polyhydroxybutyrate, polyurethanes, polyesters, styrene polymers, polyvinyl alcohol, polyacrylic acid, polyethylene oxide, their copolymers, blends and copolymer blends, combinations of the above, and the like. Suitable solvents include, but are not limited to, acetone, ethyl acetate, tetrahydrofuran (THF), chloroform, methyl ether ketone, methanol, ethanol, isopropanol, hexane, water, and combinations thereof.

In one example, the coating layers comprise a first therapeutic agent such as camptothecin, rapamycin, a rapamycin derivative, or a rapamycin analog such as everolimus or zotarolimus. Coating layers comprise a carrier layer of a predetermined thickness. In one embodiment, the thickness of the coating is selected based on expected degradation rates of the coating layer, while in other embodiments, the thickness is selected based on the drug maintained in place between the stent surface and the coating layer. In another embodiment, the thickness of the coating layer is variable over the length of the stent framework. For example, over one span of the stent framework, the coating layer is 2 micrometers thick, while in a second span of the stent framework, the coating layer is 4 micrometers thick. Drug or coating elution refers to the transfer of a material from drug coating 240 to the surrounding area or bloodstream in a body. The amount of drug eluted is determined as the total amount of therapeutic agent excreted out of drug coating 240, typically measured in units of weight such as micrograms, or in weight per peripheral area of the stent. In another embodiment, the concentration of the therapeutic agents in either drug layers or barrier layers are modulated to provide a predetermined drug-release profile.

Figure 3:
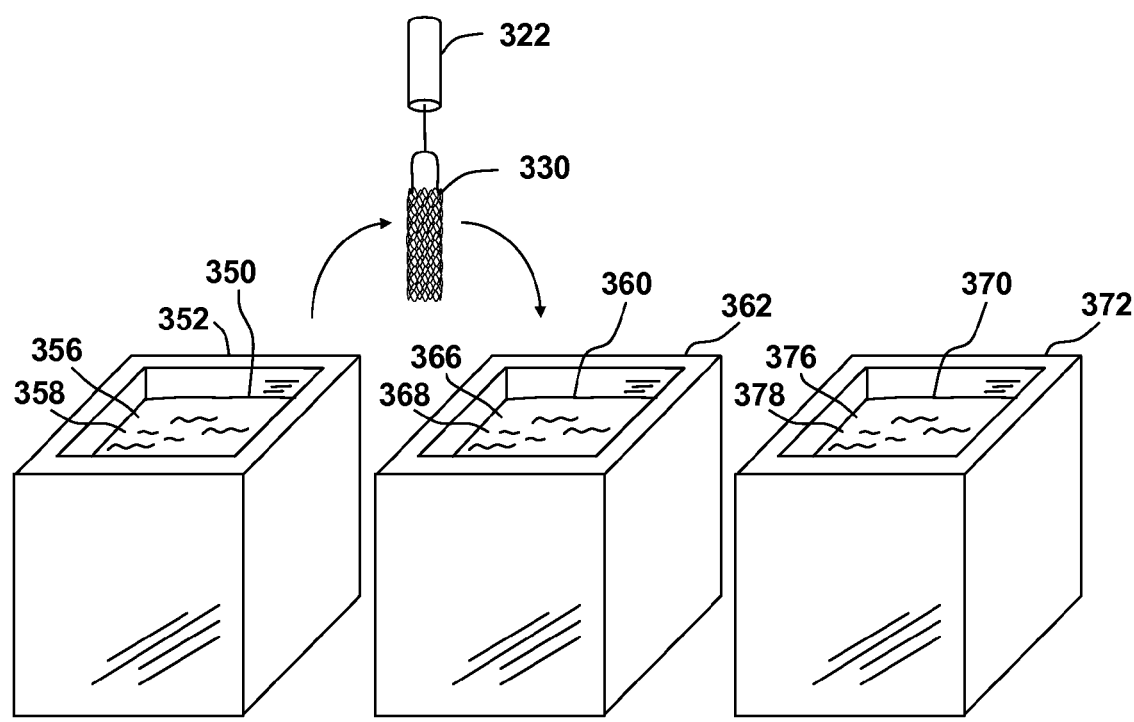
FIG. 3 is an illustration of a system for applying a coating on a stent, in accordance with one embodiment of the current invention.

FIG. 3 shows an illustration of an example system for applying a drug coating on a stent, in accordance with one embodiment of the current invention at 300. Drug coating system 300 includes a first solution 350 in a first tank 352, a second solution 360 in a second tank 362, and a mechanism 322 such as a mandrel, a clamp, or a tether for holding and transporting stents in and out of a tank either manually or automatically. Multiple stent frameworks 330 are readily accommodated for dipping and drying in a batch or continuous batch process.

For example, first solution 350 includes a first therapeutic agent 356, and a first solvent 358. Stent framework 330 can be dipped into first solution 350 and dried, for example, by positioning dipped stent framework 330 in air or in an oven and evaporating first solvent 358 to form a drug layer. Minimizing the solids content of first solution 350 can lower the viscosity, so that uniform coating and minimal or no bridging occurs across the apertures of stent framework 330. Alternatively, first solution 350 can be ultrasonically sprayed, electrostatically sprayed, or applied via micro-droplet deposition, supercritical fluids, focused acoustic beams, or piezo injectors.

Second solution 360 includes second therapeutic agent and a second solvent 368. Stent framework 330 with the first laminated drug layer can be dipped into second solution 360 and dried, for example, by positioning dipped stent framework 330 in an oven or in air for high throughput and evaporating second solvent 368 to form a therapeutic agent layer. Second solution 360 may include a second therapeutic agent 366 dissolved into second solvent 368. Low viscosity for minimizing bridging and webbing across the apertures of stent framework 330 can be obtained by minimizing the solids content of second solution 360. Alternatively, second solution 360 can be ultrasonically sprayed, electrostatically sprayed, or applied via inkjet technology. After application of first layer of therapeutic agent, an intermediate or barrier layer may be applied.

A third solution 370 in a third tank 372 includes a third solvent 378 in certain embodiments. Third solution 370 may include a third therapeutic agent 376 dissolved in third solvent 378. In one example, third solvent 378 is the same as first solvent 358, and third therapeutic agent 376 is the same as first therapeutic agent 356, though at a higher or a lower concentration than first therapeutic agent 356 in first solution 350. In this case, the concentration of third therapeutic agent 376 disposed on stent framework 330 can be higher or lower than previously coated and dried drug layers. The concentration of first therapeutic agent 356 in the drug layers can be modulated to provide a predetermined drug-release profile.

In another example, third solvent 378 is the same as second solvent 368, and third therapeutic agent 376 is the same as second therapeutic agent 366 though at a higher or a lower concentration than second therapeutic agent 366 in second solution 360. The concentration of third therapeutic agent 376 disposed on stent framework 330 can be higher or lower than previously dipped and dried barrier layers, so that the concentration of second therapeutic agent 366 in the barrier layers can be alternated to provide a predetermined drug-release profile for second therapeutic agent 366 from a coated stent when deployed in a body.

In another example, more than one therapeutic agent may be formulated in each of the solutions and applied as specified in the aforementioned example.

FIG. 4 shows a flow diagram of a method of manufacturing a coated stent, in accordance with one embodiment of the present invention at 400. Manufacturing method 400 includes various steps to form a coating on a stent framework.

A coating is formed with at least one carrier and at least one therapeutic agent at step 410. The coating is any liquid coating to be applied to a stent framework for the provision of therapeutic or diagnostic benefits. The concentration of the therapeutic agent within the carrier, termed the "coating concentration," is in one embodiment, greater than a therapeutic concentration. In such an embodiment, the therapeutic agent is dispersed within the carrier at the coating concentration such that the therapeutic agent is substantially evenly distributed throughout the carrier so that any concentration gradient across the volume of the carrier is reduced or minimized.

The coating is applied to a stent framework at step 420. The coating can be applied using any appropriate technique, such as dipping, spraying, ultrasonic spraying, electrostatic deposition, or the like. After applying the coating including the carrier and therapeutic agent to the stent, the coated stent is dried at step 430. The coated stent can be dried using any appropriate technique, including the application of heat. Therapeutic agents do not dry at the same rate as carriers, and drying the coated stent results in forming a coated stent with the at least one therapeutic agent not substantially evenly distributed within the carrier, at step 440. In other words, during steps 430 and 440, although the total volume of therapeutic agent remains substantially constant, the distribution varies resulting in the formation of a concentration gradient of therapeutic agent within the carrier. In one example, the concentration of therapeutic agents increases with distance away from the stent frame. The concentration, in one embodiment, describes a concentration gradient. In one example, the concentration gradient describes a substantially hyperbolic distribution, while in other examples, the concentration gradient describes a substantially parabolic distribution. In other embodiments, the concentration gradient is linear, geometric, or exponential. In one embodiment, drying the coated stent includes an incomplete dry so that the coated stent remains at least partially wet. In another embodiment, at least a portion of the solvent remains within the coating during the processing and/or drying.

A portion of the applied coating is removed at step 450. The applied coating can be removed using an appropriate technique, including but not limited to, application of a predetermined solvent for a predetermined time. The solvent and time span are determined responsive to the carrier and therapeutic agent. Removing the portion of the applied coating can include removing only the therapeutic agent from a washed zone 670 (FIG. 6C) of the stent or removing the therapeutic agent with the carrier from the stent framework. A washed zone is a region of the coated stent where a substantial portion of a therapeutic agent has been removed from a carrier. The therapeutic concentration zone 680 (FIG. 6C) remaining after the removal of the portion of the therapeutic agent includes a concentration of therapeutic agent, and the therapeutic concentration zone separates the washed zone from the stent framework. Each of the washed zone and therapeutic concentration zone are, in one embodiment, substantially circumferential.

In addition, the removal of the portion of the applied coating results in forming a coated stent with at least one therapeutic agent substantially evenly distributed within the carrier, step 460. Specifically, the portion of the applied coating with the highest concentration of the therapeutic agent is removed with the solvent. In one embodiment, a majority of the therapeutic agent is removed from the stent. In one embodiment, the solvent is acetonitrile. In other embodiments, the solvent is water. In another embodiment, the solvent is a saline solution. Depending on the solvent and carrier interaction, a portion of the carrier is removed with the therapeutic agent. If a portion of the carrier is removed with the therapeutic agent, the outer diameter of the coating will be reduced by a greater degree than if only therapeutic agent is removed by the solvent.

The predetermined time can be any appropriate span depending on the solvent and carrier and therapeutic agent. In one embodiment, the predetermined time span is between 1 and 5 seconds. In another embodiment, the time span is between 2 and 10 seconds. In another embodiment, the time span is between 1 and 5 minutes. In another example, the time span is between 6 and 12 hours. Any time span in between these enumerated spans, and outside these enumerated spans can be used.

In one embodiment, as the therapeutic agent is removed from the coating, the therapeutic agent becomes dispersed throughout the solvent, and in one embodiment, the dispersed therapeutic agent is recovered from the solvent. In one example, the therapeutic agent precipitates out of the solvent. In another example, the solvent is evaporated off, leaving the therapeutic agent.

Figure 5A:
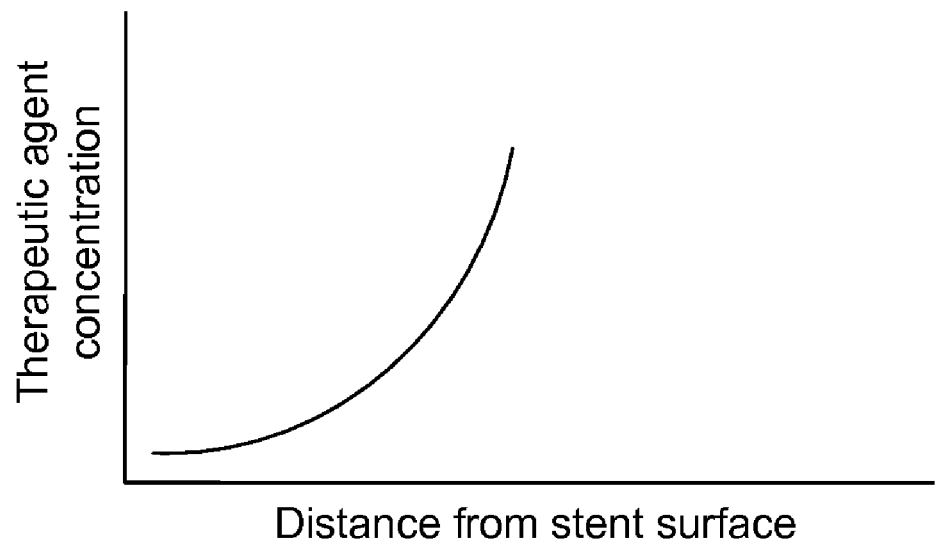
FIG. 5A and FIG. 5B are graphs illustrating therapeutic agent concentration, in accordance with one embodiment of the current invention.
Figure 5B:
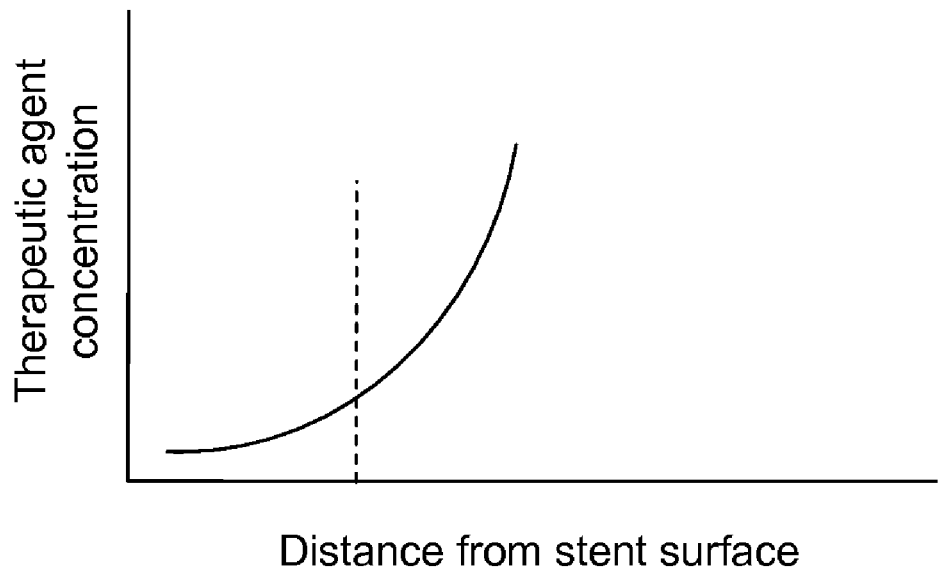

For example, FIG. 5A illustrates an exemplary gradient curve illustrating the distribution of therapeutic agent within a carrier, prior to removing a portion of the therapeutic agent, as in step 450. The x-axis represents distance from a stent surface, while the y-axis represents concentration. As shown in FIG. 5A, the concentration rapidly increases with distance from the stent surface. FIG. 5B illustrates the gradient curve of FIG. 5A, with a dotted line indicating a portion of the coating that is removed from the outer edges of the carrier. Thus, to the left of the dotted line in FIG. 5B, or the portion of the therapeutic agent that remains after removal of the portion, the concentration of therapeutic agent within the carrier is substantially consistent, indicative of a substantially even distribution of therapeutic agent within the carrier. In one embodiment, the term substantially consistent means that the difference between concentrations across the carrier is less than or equal to about twenty-five percent of the highest concentration.

Figure 6B:
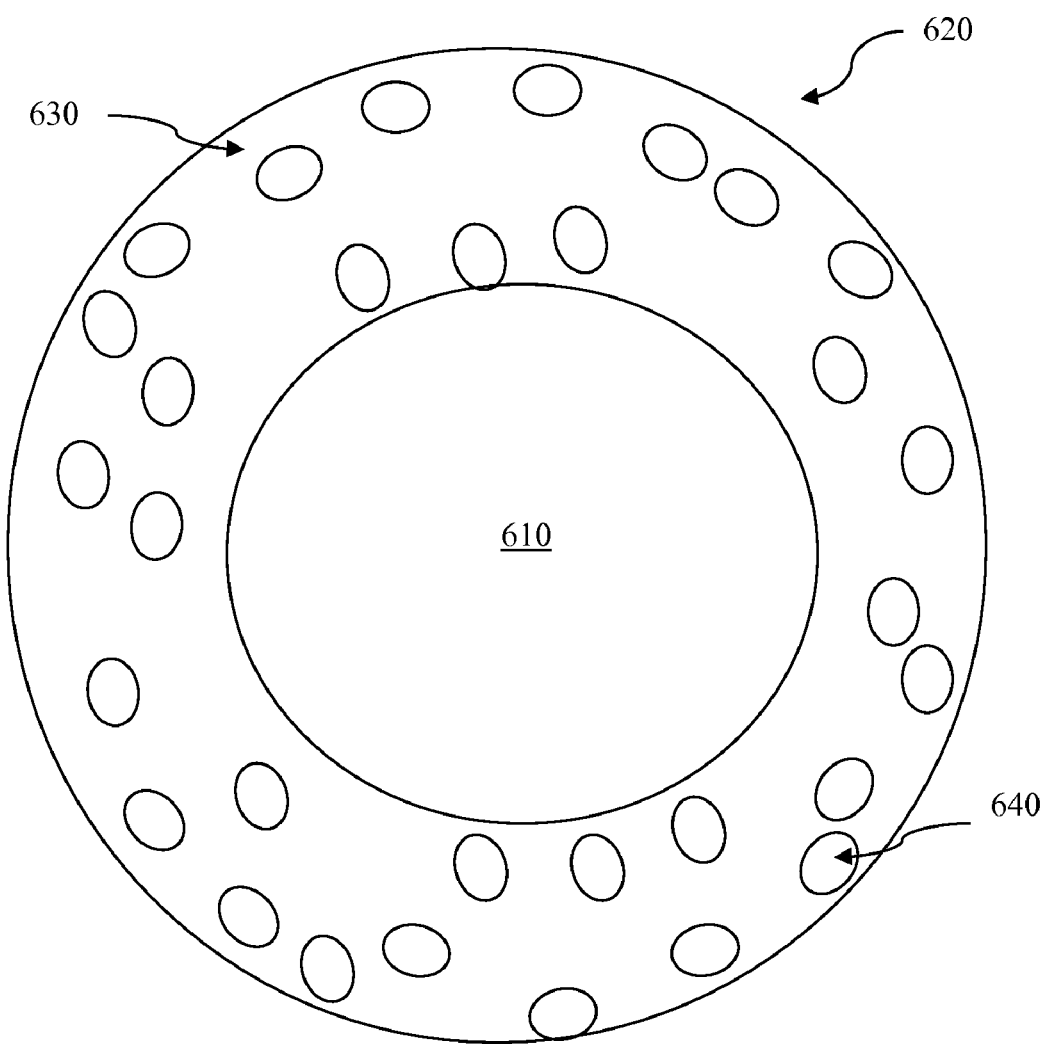
Figure 6C:
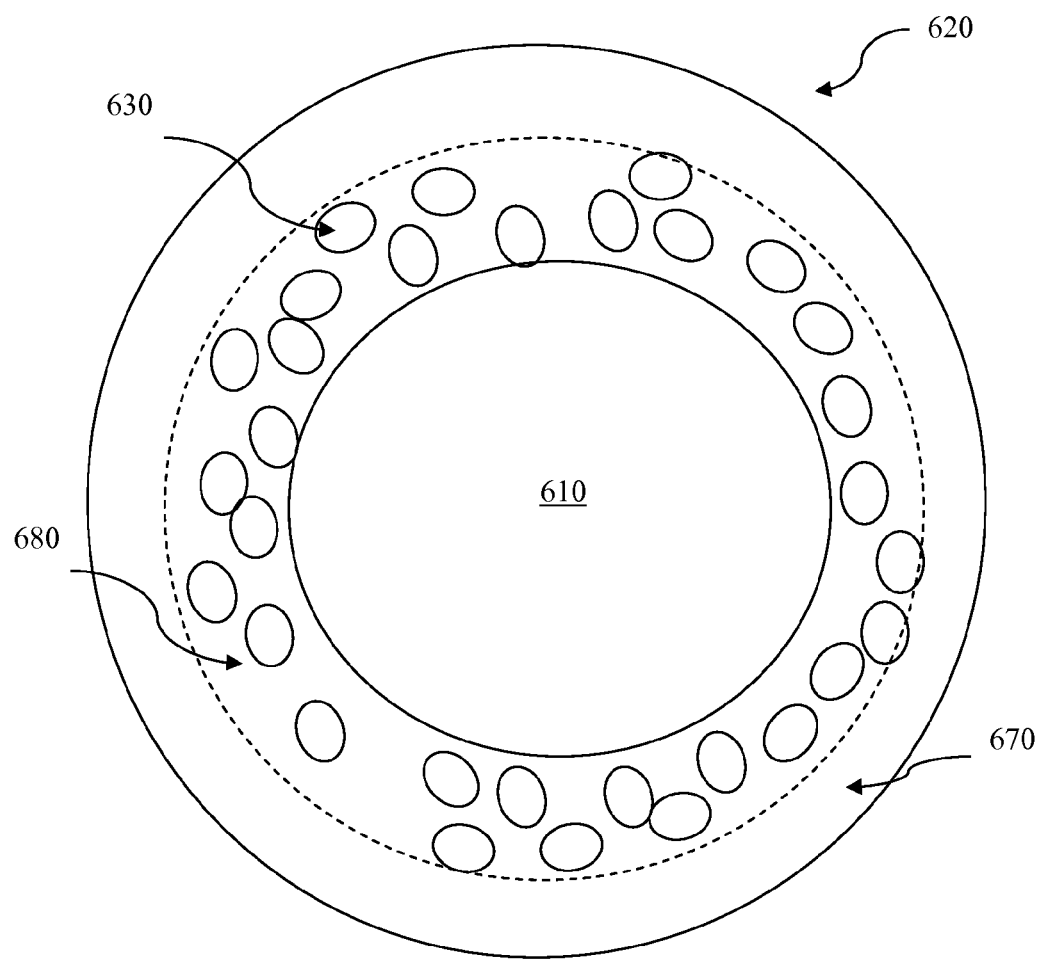

FIG. 6A illustrates a cross section of a stent framework 610, including a coating 620. Coating 620 includes a carrier 630 and a therapeutic agent 640. As seen in FIG. 6A, the therapeutic agent 640 is distributed unevenly. The area where the therapeutic agent is distributed unevenly is defined as a high concentration zone. The high concentration zone 660 surrounds a therapeutic concentration zone 670 wherein the therapeutic agent is substantially evenly distributed. Zone line 650 separates the high concentration zone 660 from the therapeutic concentration zone 670. Zone line 650 is not a physically defined boundary, and is included for ease of description. In one embodiment, the high concentration zone is separated from the therapeutic concentration zone with a gradient. In one embodiment, FIG. 6A illustrates the dried coated stent. FIG. 6B illustrates a cross section of stent framework 610 with coating 620. Coating 620 still comprises a carrier 630 and therapeutic agent 640, but the concentration of therapeutic agent is substantially consistent throughout the carrier 630, so that the high concentration zone 660 has been substantially removed, leaving only a carrier 630 comprising therapeutic agent at a concentration similar to the concentration within the therapeutic concentration zone. washed zone FIG. 6C illustrates the stent including a washed zone 670. The washed zone 670 is a region that has a majority of therapeutic agent removed from the carrier. The stent further includes therapeutic concentration zone 680 separating the washed zone 670 from the stent framework 610. In one embodiment, the washed zone 670 is formed by removal of therapeutic agent from the high concentration zone 660 (FIG. 6A).

In one embodiment, a method for manufacturing a coated stent includes forming a coating with at least one carrier and at least one therapeutic agent. The formed coating is applied to the stent, and the coated stent is dried, forming a coated stent with a high concentration zone separated from the stent framework by a therapeutic concentration zone. A portion of the dried coated stent is removed, such as with a solvent, forming a coated stent with the therapeutic agent distributed within the carrier. Removing the portion of the applied coat, in one embodiment, includes removing at least a portion of the therapeutic agent from the high concentration zone. In one embodiment, removing at least a portion of the therapeutic agent from the high concentration zone comprises removing a sufficient amount of therapeutic agent so that the concentration of therapeutic agent throughout the carrier is substantially equal to the therapeutic concentration. In one embodiment, the high concentration zone becomes a washed zone after the portion of the coating is removed.

In determining the amount of therapeutic agent to be included in the formed coating, the desired therapeutic dosage should be considered, and the therapeutic concentration will be less than the coating concentration. In one embodiment, the formed coating comprises a toxic amount of therapeutic agent.

Although the present invention applies to cardiovascular and endovascular stents, the use of drug coatings may be applied to other implantable and blood-contacting biomedical devices such as coated pacemaker leads, microdelivery pumps, feeding and delivery catheters, heart valves, artificial livers and other artificial organs.

While the invention has been described with reference to particular embodiments, it will be understood by one skilled in the art that variations and modifications may be made in form and detail without departing from the spirit and scope of the invention.

What is claimed is:

1. A method of manufacturing a coated stent comprising:
    determining a therapeutic concentration;
    determining a coating concentration, the coating concentration greater than the therapeutic concentration,
    forming a coating, the coating including at least one carrier and at least one therapeutic agent, wherein forming a coating comprises distributing the therapeutic agent within a carrier at the coating concentration and wherein the at least one therapeutic agent is substantially evenly distributed within the carrier;
    applying the formed coating to the stent;
    drying the coated stent;
    removing a portion of the dried applied coat wherein removing a portion of the applied coat reduces the thickness of the coating; and
    forming a coated stent wherein the at least one therapeutic agent is substantially evenly distributed within the carrier wherein the therapeutic agent is distributed within the carrier at the therapeutic concentration.

2. A method of manufacturing a coated stent comprising:
    determining a therapeutic concentration;
    determining a coating concentration, the coating concentration greater than the therapeutic concentration,
    forming a coating, the coating including at least one carrier and at least one therapeutic agent, wherein forming a coating comprises distributing the therapeutic agent within a carrier at the coating concentration and wherein the at least one therapeutic agent is substantially evenly distributed within the carrier;
    applying the formed coating to the stent;
    drying the coated stent;
    removing a portion of the dried applied coat wherein removing a portion of the applied coat reduces an outer diameter of the coated stent; and
    forming a coated stent wherein the at least one therapeutic agent is substantially evenly distributed within the carrier wherein the therapeutic agent is distributed within the carrier at the therapeutic concentration.

* * * * *